United States Patent [19]
Amirav et al.

[11] Patent Number: 6,096,178
[45] Date of Patent: Aug. 1, 2000

[54] ELECTROLYZER DEVICE FOR THE OPERATION OF FLAME IONIZATION DETECTORS

[75] Inventors: Aviv Amirav, 5 Hayaar Alley, Ramat Hasharon 45269; Nitzan Tzanani, Tel-Aviv, both of Israel

[73] Assignee: Aviv Amirav, Ramat Hasharon, Israel

[21] Appl. No.: 09/138,707

[22] Filed: Aug. 24, 1998

[51] Int. Cl.⁷ .............................. C25B 9/00; C25C 7/00; C25D 17/00

[52] U.S. Cl. ............................ 204/274; 204/278; 62/3.4; 422/54

[58] Field of Search ..................... 204/274, 278; 422/54; 436/177; 136/203; 62/3.2, 3.3, 3.4, 3.5, 3.6, 3.7

[56] References Cited

U.S. PATENT DOCUMENTS

| | | | |
|---|---|---|---|
| 3,212,274 | 10/1965 | Eidus | 62/3.2 |
| 4,388,411 | 6/1983 | Lovelock | 436/149 |
| 4,822,469 | 4/1989 | Shimomura et al. | 204/230 |
| 5,037,518 | 8/1991 | Young et al. | 204/230 |
| 5,244,558 | 9/1993 | Chiang | 204/241 |
| 5,628,885 | 5/1997 | Lin | 204/228 |
| 5,741,711 | 4/1998 | Amirav et al. | 436/154 |
| 5,858,185 | 1/1999 | Christian | 204/272 |

OTHER PUBLICATIONS

Rowe, D.M. CRC Handbood of Thermoelectrics. 1995, CRC Press, pp. 617–619. No month available.

*Primary Examiner*—Kathryn Gorgos
*Assistant Examiner*—Wesley A. Nicolas
*Attorney, Agent, or Firm*—McAulay Nissen Goldberg & Kiel, LLP

[57] ABSTRACT

The invention provides a water electrolyzer device for generating a premixed hydrogen and oxygen gas mixture and for directing said gas mixture into a flame ionization detector, the device including a water container for performing water electrolysis; an electrode for passing electrolysis current in the water; and a water mist and vapor pressure management system for the elimination of water mist and reduction of the water relative humidity below the saturation point, the system being located between the water electrolyzer and the flame ionization detector. A method based on water electrolysis for the provision of a combustible gas mixture for the operation of a flame ionization detector is also provided.

13 Claims, 1 Drawing Sheet

ELECTROLYZER DEVICE FOR THE OPERATION OF FLAME IONIZATION DETECTORS

FIELD OF THE INVENTION

The present invention relates to the field of flame ionization detection, and more particularly, the invention is concerned with an electrolyzer-powered flame ionization detector.

BACKGROUND OF THE INVENTION

The flame ionization detector (FID) is the most widely used detector for gas chromatography (GC) and is also used as a stand-alone monitor of the total hydrocarbon concentration in air. Although very effective, the FID typically consumes 30 ml/min of hydrogen, 30 ml/min of helium make-up gas and 300–400 ml/min of pure air. Clearly, it is highly desirable to eliminate these gases, their cylinders, pneumatics and safety hazards from the FID and GC. Recently, a new type of FID was developed, based on the provision of a low flow rate of an unseparated gas mixture of oxygen and hydrogen, provided by a simple water electrolyzer. This electrolyzer-powered FID (EFID) considerably simplifies the gas logistics of GC-FID, improves its operational safety, reduces the cost of analysis and significantly improves its transportability. The water electrolyzer of the EFID contains a special chamber or canister, filled with either silica gel or molecular sieve particles, that serves for the adsorption of the water vapor. These powders or particles have a limited water capacity and need periodic manual replacement that may also result in leaks if some powder dust finds its way to the o-ring seal. Furthermore, the standard water electrolyzers are hard to automate and thus suffer from limited continuous operation time that is undesirable in a modern laboratory environment. The major reason for this situation is that while water is an easily transferable liquid, the needed solid water adsorbing material requires manual replacement periodically before its saturation and thus precludes the full automation of the EFID.

In a standard water electrolyzer, the oxygen and hydrogen gas mixture are formed as several thousand small bubbles per second and thus are saturated with water vapor and carry a large amount of water mist. This water mist is very harmful to the long-term operational stability of the electrolyzer, as the potassium hydroxide in the water tends to clog the gas flow path when the water evaporates. In addition, excessive loss of potassium hydroxide may require its undesirable periodic replenishment. Furthermore, when the water vapor itself condenses on the gas tube, it temporarily clogs the gas tube and can induce severe FID background noise and even result in total flame extinguishing. The water electrolyzer of the present invention is based on the elimination of the water mist and the reduction of the relative humidity to well below 100%, preferably to around 50%, in order to eliminate and solve the above-described problems.

The process of water mist elimination and humidity reduction can be achieved in several ways, including:

a) Two cells can be used, with a standard water-adsorbing material, a heating unit for each cell, and an air pump that can be directed to each cell. When a given cell is close to saturation with water, the electrolyzer gases can be directed through the second cell and the saturated cell is heated while room air is pumped through it to desorb the previously adsorbed water from it. Afterwards, it is closed, cooled back to room temperature and is ready for future service. The water adsorbing material also adsorbs the potassium hydroxide contained in the water mist. The need for two cells is only to enable full automation and relatively uninterrupted EFID operation. This arrangement is useful but somewhat complex, increasing the cost of the water electrolyzer and requiring some periodic addition of potassium hydroxide.

b) A freon or hydrocarbon-based, small refrigerator can be built with a miniature closed refrigeration cycle unit for water mist and vapor recirculation. This is a possible approach, but may be too costly; it also suffers from reduced reliability.

c) A miniaturized refrigeration unit, based on a Peltier semiconductor solid state device, can be built for water mist elimination and vapor pressure reduction. This unit seems to offer the ideal solution for the water mist and vapor management requirements. The basic idea is that the Peltier element will cool a gas condenser element located above the electrolyzer, so that the water mist and vapor will condense, liquefy and recirculate back to the water reservoir below. In this way, a mist-free gas mixture, with a relative humidity of about 50%, will be generated if the cooled condenser temperature is 10° C. below room temperature. Therefore, the water electrolyzer of the present invention was built around a Peltier-based water mist and vapor recirculating and management system.

SUMMARY OF THE INVENTION

A novel water electrolyzer has therefore been developed, characterized and tested that is ideally suited for delivering the total gas supply of an EFID. The novel water electrolyzer of the present invention is uniquely characterized by having no replaceable water-adsorbing material and, as such, features full automation compatibility. In addition to this feature, it has a relatively large water reservoir for achieving long and uninterrupted EFID operation with a short initial operational response time and advanced safety features. It is highly reliable with no moving parts, has a low water and energy consumption, can require only one simple power supply, provides a very stable combustible gas mixture flow rate and includes protection against the adverse effects of the alkali base found in the water.

Thus, the present invention provides a water electrolyzer device for generating a premixed hydrogen and oxygen gas mixture and for directing said gas mixture into a flame ionization detector, said device comprising water container means for performing water electrolysis; electrode means for passing electrolysis current in the water; and a water mist and vapor pressure management system for the elimination of water mist and reduction of the water relative humidity below the saturation point, said system being located between said water electrolyzer and said flame ionization detector.

The invention further provides a method based on water electrolysis for the provision of a combustible gas mixture for the operation of a flame ionization detector, said method comprising the steps of generating, by means of a water electrolyzer, a premixed, combustible hydrogen and oxygen gas mixture; reducing water mist and relative humidity below saturation level, without the use of replaceable adsorbing material, in order to prevent water condensation in the flow path of said gas mixture to said flame ionization detector; and directing flow of combustible gas mixture into said flame ionization detector.

BRIEF DESCRIPTION OF THE DRAWING

The invention will now be described in connection with certain preferred embodiments with reference to the following illustrative FIGURE, so that it may be more fully understood.

With specific reference now to the FIGURE in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawing making apparent to those skilled in the art how the several forms of the invention may be embodied in practice.

DETAILED DESCRIPTION OF PREFERRED EMBODIMENTS

Figure 1:
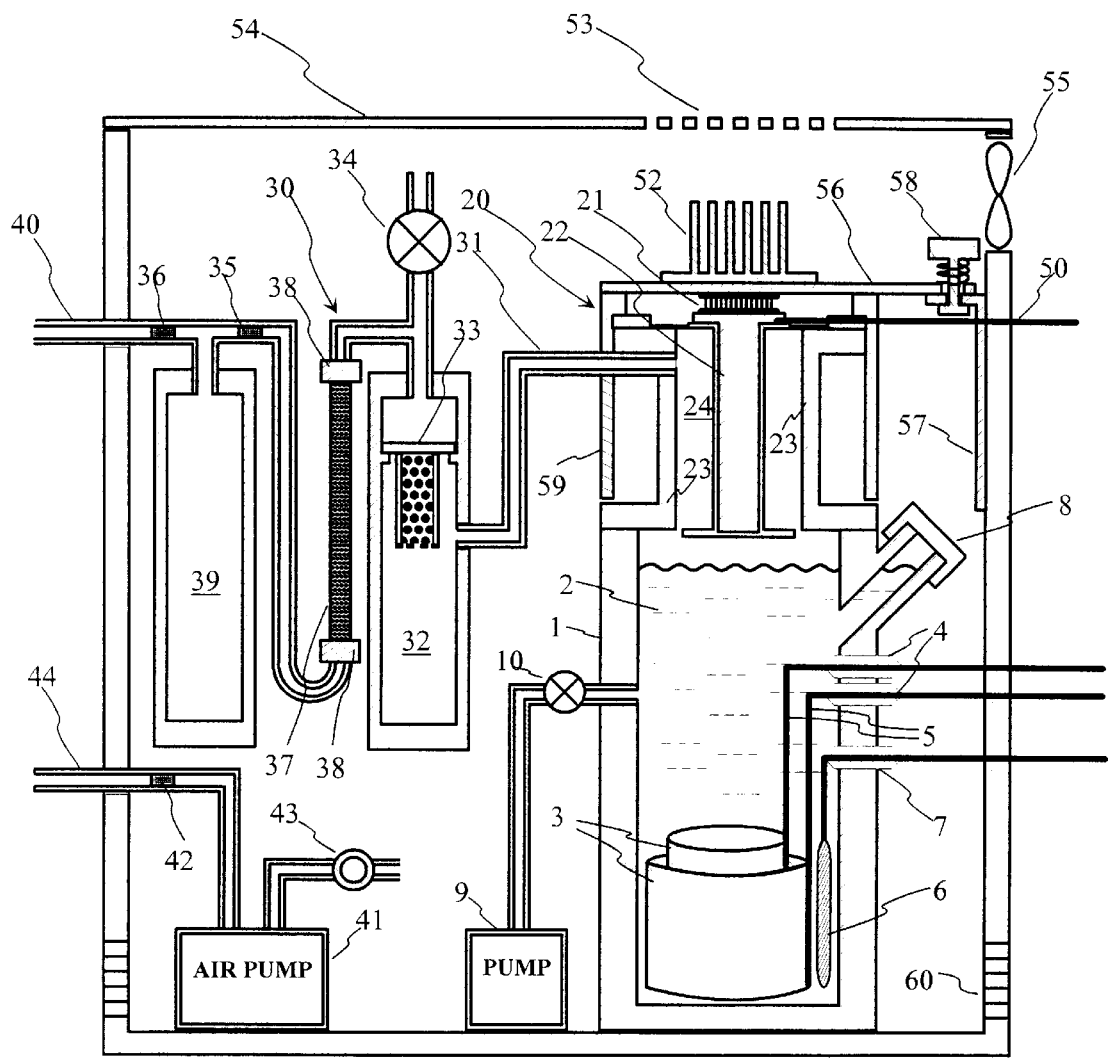
FIG. 1 is a schematic, cross-sectional view of a water electrolyzer according to the present invention.

Referring to FIG. 1, there is shown a relatively large water reservoir 1, filled with about 500 ml of water 2 mixed with 15 grams of potassium hydroxide, enabling the continuous, uninterrupted EFID operation for one month at an electrolysis current of 2 Ampere. Ti water electrolyzer parts are made of polypropylene, which is compatible with the basic water solution. The dimensions of the water reservoir are 100 mm OD and 76 mm ID. The wall thickness is calculated to be able to handle a gas pressure of over 4 atmospheres. A pair of electrodes 3 for electrolysis are disposed inside the reservoir and are made of, e.g., 0.25 mm thick nickel mesh mounted on polypropylene cylinders in which there are many large holes. The electrodes are mounted on a pair of stainless steel 316 current feedthroughs 4, electrically connected with 2×1.3 mm diameter stainless steel 316 wires 5. An additional stainless steel wire 6 serves as a water level monitoring device and is mounted on an electrical current feedthrough 7. The water level reduction below this monitor can be sensed by a sudden increase in the electrical resistivity to the nearby electrode. Alternative devices and methods for monitoring the water level can be based on using a Coulomb meter (Ampere hour monitoring) or monitoring the electrolysis voltage. This voltage initially reduces over time, since water electrolysis increases the potassium hydroxide concentration. However, when the electrolysis electrode is exposed, the voltage begins to rise and a return to the initial voltage value (or to a given higher target voltage) may be used as an indication of the need to replenish the water. It was also found that the electrical contacts used, such as banana plugs, should preferably be gold-coated for reduced contact potential.

Water is added manually from the manual water input port 8, which is properly plugged and sealed with an O-ring. All of the O-rings in the electrolyzer are made from ethylene-propylene-diene monomer (EPDM), for enhanced compatibility with the basic water solution. The water can also be automatically replenished by the small water pump 9 that delivers pure water (18.3 megaohm purified water, with or without an added small concentration of KOH) from an external water container (not shown) through an externally controlled solenoid valve 10.

The electrolyzer-produced oxygen and hydrogen gas mixture, combined with the water mist and vapor, enters the water mist and vapor recirculating and management system 20. A solid state Peltier cooling unit 21 serves to cool a stainless steel 316 cylinder 22 filled with an aluminum or copper rod that provides efficient heat transfer to the Peltier cooling unit 21. Cylinder 22 has a stainless steel mounting flange with a thin separating gap of 1 mm thickness for the reduction of its thermal conductivity, as schematically shown in the Figure. The volume between the cooled cylinder 22 and the external polypropylene walls 23 has a relatively large gap of 6 mm. Volume 24, with its relatively large cross-sectional area, is intended to slow down the gas motion for its effective temperature equilibration with cylinder 22. Thus, the structure is aimed at slowing down the upward velocity of the water mist to enable it to effectively cool down for increased mist trapping and vapor condensation efficiency.

The generated gas mixture, with reduced relative humidity, flows into a gas cleaning and flow rate stabilization system 30. The gas mixture first flows via a transfer Teflon tube 31 (1/8" OD, 1/16" ID), to a special polypropylene container 32 containing a coarse KOH filter element 33. Container 32 serves to accommodate excess water in case of improper water management system operation, and it also reduces the propagation of potassium hydroxide beyond it. Any drops of water will fall into container 32 and then be vaporized without bubble or mist formation. Container 32 also includes a check valve 34, tuned to open at, e.g., 1.7 atmospheres, while the normal operational pressure is about 0.5 atmosphere. The check valve 34 is positioned after and above the coarse grain adsorbing material (e.g., molecular sieves, 3 mm diameter grains) covered with a sintered glass filter element to protect it from most of the potassium hydroxide dust.

A major and unexpected problem encountered with this electrolyzer concerns the harmful effect of potassium hydroxide dust that clogs the frit flow stabilizing element 35 and largely increases the EFID noise. A portion of the water mist completely or mostly evaporates, leaving its nonvolatile content of potassium hydroxide as a fine-particled dust. This potassium hydroxide is essential for the reduction of the water resistivity in order to enable the water electrolysis; however, it presents a major problem in the mist and needs to be completely eliminated. The problem of potassium hydroxide dust is further exacerbated by its tendency to pass through the coarse glass frit and even the fine stainless steel frits until it eventually enters the FID and induces major noise spikes, in addition to a gradual clogging of the frits 35 and 36. The complete elimination of this problem is achieved by the addition of an adsorption column 37. This column is based on a 1/4" Teflon tube with about 4 mm ID, filled with standard packed column gas chromatographic adsorbing material, e.g., porous alumina with 80 mesh grain size, pre-washed with water. The column was further washed several times in water, in order to eliminate any pre-adsorbed organic compounds. The Teflon tube is sealed on both sides with a stainless steel 200 mesh, mounted on a standard 1/4" tubing connection 38. Column 37 effectively adsorbs and immobilizes the potassium hydroxide dust, rendering it harmless. The adsorbing material is saturated with water and thus serves only for the removal of KOH without affecting the relative humidity of the combustible gas mixture.

The gas mixture output from column 37 flows through a standard stainless steel frit 35 (e.g., a Mott frit) specified for a 250 ml/min nitrogen flow rate under a pressure difference of 30 PSIG. The frit needs protection against the water mist since it is susceptible to clogging by the potassium hydroxide; hence, it is located downstream of the protecting adsorption column 37. The frit 35 serves two major purposes: (a) it acts as a flame arrester, further ensuring and protecting the water electrolyzer against any external flame flashback; and (b) it serves to stabilize the water electrolyzer-produced gas mixture flow rate. The stabilization of the flow rate is desirable in order to reduce the EFID background noise fluctuations and enhance its sensitivity. While the electrolysis current controls the long term gas mixture flow rate stability, due to the nature of gas bubble formation, the short term flow rate stability must also be ensured. The frit 35 increases the gas mixture pressure in the water electrolyzer and container 32 and increases the time constant of flow rate fluctuations. Thus, frit 35 acts as the pneumatic analog of an electronic RC noise filter.

To further enhance the feature of flow rate stabilization, it is advantageous to add an additional polypropylene gas container 39 and a second frit 36, identical to frit 35. The hydrogen and oxygen stochiometric gas mixture flows from the gas output Teflon tube 40 into the GC, where it is connected to the central FID hydrogen and make up gas tube. A small air pump 41 is capable of delivering about 100–150 ml/min of air through a frit flow restrictor 42. The air pump 41 delivers room air, that can be partially filtered from dust particles and hydrocarbons by the filter 43, into the GC air tube 44. Air pump 41 is intended for use during the solvent elution time, when megabore (0.53 mm ID) columns are used, in order to prevent solvent-induced flame extinguishing. It can also help to maintain the flame under a high GC carrier gas flow rate (above 8 ml/min) which otherwise tends to extinguish the flame. Since the flame mostly consumes its own pure oxygen, the presence of small amounts of methane and other hydrocarbons in room air has only a small adverse effect on the EFID sensitivity. The air pump serves the additional purpose of adding room air just prior to the EFID flame ignition, to suppress the ignition audio noise. Thus, the automated ignition cycle must also include the addition of room air by the pump a few seconds prior to turning on the flame.

It has been found that the optimal electrolysis current is 2 Ampere, which produces 23 ml/min of the hydrogen and oxygen gas mixture. At this flow rate, the initial time constant for flame ignition and achieving stable EFID operation can be 10 minutes. This time constant is approximately ½ the empty volume 24 in the electrolyzer and stabilization containers 32 and 39, divided by the flow rate of 23 ml/min. Accordingly, a total flow stabilization volume of 460 ml results in a 10 minute EFID time constant. In order to further speed up the flame ignition and stabilization, the initial electrolyzer current can be 2.5 A for about 10 minutes and then be reduced to 2 A. At an electrolyzer current of 2.5 A, the EFID sensitivity can be slightly improved, but the rate of water consumption will be higher.

The proper operation of the Peltier cooling unit 21 is central to the successful operation of the electrolyzer of the present invention. Accordingly, a thermocouple temperature measurement wire 50 is added to measure the actual temperature difference between the Peltier cooled cylinder 22 and the room temperature. A temperature difference of 2° C. is required to prevent water condensation in the gas mixture flow tube 31, while a 4° C. temperature difference is required to further suppress the EFID electrical noise. Since the room temperature may fluctuate and the temperature at the vicinity of the GC may be hotter, depending on the GC oven temperature, a safe Peltier-induced temperature gradient is at least 8° C. and preferably 10° C. A larger temperature gradient may restrict the laboratory operational temperature due to water freezing problems. Thus, the target temperature difference is 10° C.

The task of achieving a 10° C. temperature gradient is not trivial and requires attention to several features. The Peltier element cools cylinder 22 by pumping the heat to its upper surface. This excess heat must be properly dissipated back to the surrounding room. The simplest way to achieve this is to cool the upper Peltier cooling unit 21 by positioning an air-cooled radiator element 52 below a mesh opening 53 in the electrolyzer external box 54 for improved air convection. The cooling of the Peltier unit 21 is largely improved by using forced-air cooling with a small air blower or fan 55. A computer chip cooling fan that consumes 0.5 Watts can be used for this purpose. A very powerful fan is not desirable, as in addition to cooling the upper Peltier cooling unit, it will also heat the cooled surface of the upper electrolyzer water mist and vapor management system 20. The forced air cooling works very effectively but it has two drawbacks: (a) it requires a further 5 or 12V power source; and (b) it is a moving part that may limit the mean time between failures and robustness of the system.

In order to eliminate the forced air fan, the static air radiator efficiency had to be improved by coupling it to the surface of electrolyzer external box 54. This was achieved by using a 5 mm thick slab 56 of copper that slides on top of another copper piece 57, which is mounted with three screws to the electrolyzer box external air cooled surface. In this way, the copper slab effectively transfers the Peltier generated heat into the large surface area of the electrolyzer box, where it is then dissipated into the room air. Since the Peltier unit 21 is delicate and can be ruined by pushing the sliding copper slab 56, this sliding bar and the copper angled piece 57 are connected with a tunable force of springs by an arrangement 58. In this way, the disassembly of the water mist and vapor recirculating and management system can be performed without disassembling the Peltier cooling unit.

It has also been found that the cooled cylinder 22 was heated by the room air flowing around the external polypropylene surface 23. Thus, a thermally insulating polypropylene cover 59 was added and a further layer of packaging material for thermal insulation is added inside unit 59, or on the outside of unit 23. Between the thermal insulation unit 59 and the cooled cylinder 22 there is a small groove, two mm deep, in its stainless steel metal flange. This groove enables the transfer of the thermocouple (50) wires and the electrical connections of the Peltier cooling element 21, and also serves to drain the water formed by the condensation of water in the room air on the outer surface of the cooled cylinder 22.

The water electrolysis produces 1–2 watts heat, which raises the temperature of water reservoir 1. In order to properly ventilate the unit and avoid its harmful effect on the temperature of the cooling cylinder 22, several (e.g., six) 1 cm diameter holes 60 are formed at the lower portions of the external box 54, for improved ventilation of the electrolyzer.

Proper EFID electrolyzer operation requires the initiation of the Peltier cooling unit first, until a 5° C. temperature drop relative to the room temperature is achieved, and only then may the electrolysis current be turned on. Any reduction in temperature difference below this 5° C. value requires the shut-down of the unit for inspection of the cause. Under normal operating conditions, both the Peltier and electrolysis require 2 Ampere at 2.5 Volts each, resulting in a 12° C. temperature difference. For simplification of the power supply requirements, a Peltier element that could use the same current as the electrolyzer is advantageously chosen, and thus, both units will operate from a single 2 A, 5 V power supply. Furthermore, the electrolyzer should be placed away from the GC, e.g., at a distance of 20 cm, in order to avoid its harmful heating effect.

The water electrolyzer described above was optimized for the operation of FID with a premixed mixture of oxygen and hydrogen. Clearly, the water mist and vapor pressure management system can find additional use with standard hydrogen generators if the complete elimination of the water vapor is not essential, such as in the case of hydrogen generation for standard FID operation.

The water electrolyzer described above was optimized for the EFID operation without any adsorbing material. Clearly, for a few applications where the presence of water is undesirable or the quality of the water is low, water adsorbing material is needed. This water adsorbing material protects and is followed by a hydrocarbon adsorbing material (trap) to reduce the FID noise originating from the water impurities. Even in these cases, the water mist and vapor pressure management system is very useful, since it can triple the time interval before the replacement of the water adsorbing material is required.

The EFID electrolyzer electronics and software can benefit from several interlocks and constraints, such as:

1) The water electrolyzer is operated only after a 5° C. temperature difference between the cooled cylinder and room temperature is achieved. Thus, the Peltier element is the first to be turned on. Similarly, if for any reason this temperature difference requirement is not met, the electrolyzer is shut down.
2) The electrolyzer operation includes a standby position for Peltier operation without the electrolyzer, to save its initial cooling time.
3) If the water electrolyzer is turned off for more than 10 minutes, its initial electrolysis current can be 2.5 Ampere for a few predetermined minutes, before stabilizing on 2 Ampere, to speed up the equilibration time required for stable EFID operation.
4) The electrolyzer upper voltage is limited to 3.3 V. If this value is exceeded, it either indicates a problem or requires the addition of potassium hydroxide.
5) The liquid level meter controls an LED or a water pump for water addition.
6) If the flame is extinguished as indicated by the lack of EFID background current, then after some time delay, the electrolyzer current is turned off.
7) The igniter coil is turned on after several seconds of air pump operation.
8) The air pump operation time is controlled or programmed according to the anticipated solvent elution time, by the GC "start" time.

Several safety considerations were included in the design of the electrolyzer, such as: (a) the inclusion of check valve 34; (b) the inclusion of two frit flame arrestors 35 and 36 on the combustible gas line; (c) the reduction of the total volume to a minimum, to minimize energy in the unlikely event of an explosion; (d) the addition of an external ventilated box that further dampens the effect of a flame flashback; (e) the low flow rate of 23 ml/min of the electrolyzer renders it much safer than any of the known FIDs.

It will be evident to those skilled in the art that the invention is not limited to the details of the foregoing illustrated embodiment and that the present invention may be embodied in other specific forms without departing from the spirit or essential attributes thereof. The present embodiments are therefore to be considered in all aspects as illustrative and not restrictive, the scope of the invention being indicated by the claims rather than by the foregoing description, and all changes which come within the meaning and range of equivalency of the claims are therefore intended to be embraced therein.

What is claimed is:

1. A water electrolyzer device for generating a premixed hydrogen and oxygen gas mixture and for directing said gas mixture into a flame ionization detector, said device comprising:
   water container means for performing water electrolysis;
   electrode means for passing electrolysis current in the water; and
   a water mist and vapor pressure management system located between said water electrolyzer and said flame ionization detector for the elimination of water mist and reduction of relative humidity of said gas mixture below the saturation point without the use of replaceable absorbing material.

2. The water electrolyzer device according to claim 1, wherein said water mist and vapor pressure management system comprises a solid state Peltier cooling element.

3. The water electrolyzer device according to claim 2, wherein said Peltier cooling element is operative to reduce the temperature of the cooled volume by 5 or more degrees ° C. below the room temperature.

4. The water electrolyzer device according to claim 2, wherein said Peltier cooling element is cooled through heat conductivity to the electrolyzer external box surface, which surface is air cooled by heat conductivity to the room air.

5. The water electrolyzer device according to claim 1, wherein said water mist and vapor pressure management system further comprises means for the removal of dust and/or small droplets produced by the drying of water mist.

6. The water electrolyzer device according to claim 5, wherein said means for the removal of dust produced by the drying of water mist is based on porous material.

7. The water electrolyzer device according to claim 1, wherein said water electrolyzer further comprises means for measuring the amount of residual water inside said water electrolyzer, to enable replenishment thereof before its total consumption.

8. The water electrolyzer device according to claim 1, wherein said water electrolyzer further comprises means for automated water replenishment.

9. The water electrolyzer device according to claim 1, wherein said water electrolyzer further comprises check valve means, at least indirectly connected to said water container, for increased safety.

10. The water electrolyzer device according to claim 1, wherein said water electrolyzer further comprises means for stabilizing the flow rate of the output premixed oxygen and hydrogen gas mixture.

11. The water electrolyzer device according to claim 1, wherein said water electrolyzer further comprises means for provision of room air into said flame ionization detector.

12. A water electrolyzer device for generating hydrogen gas and for directing said hydrogen gas into a flame ionization detector, said device comprising:
   water container means for performing water electrolysis;
   electrode means for passing electrolysis current in the water;
   means for separating hydrogen from co-produced oxygen; and
   a water mist and vapor pressure management system located between said water electrolyzer and said flame ionization detector for the elimination of water mist and reduction of relative humidity of said hydrogen gas below the saturation point without the use of replaceable absorbing material.

13. A water electrolyzer device for generating a premixed hydrogen and oxygen gas mixture and for directing said gas mixture into a flame ionization detector, comprising:

means for generating a pre-mixed, combustible hydrogen-oxygen gas mixture;

means for reducing water mist and relative humidity below saturation level, without the use of replaceable absorbing material, in order to prevent water condensation in the flow path of the gas mixture to the flame ionization detector; and means for directing flow of combustible gas mixture into the flame ionization detector.

\* \* \* \* \*